(12) United States Patent
Ogasawara et al.

(10) Patent No.: US 6,335,458 B1
(45) Date of Patent: Jan. 1, 2002

(54) INTERMEDIATE COMPOUNDS IN THE SYNTHESIS OF THE A RING MOIETY OF 2-SUBSTITUTED VITAMIN D DERIVATIVES

(75) Inventors: Kunio Ogasawara; Michiyasu Takahashi, both of Miyagi (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/623,163

(22) PCT Filed: Feb. 25, 1999

(86) PCT No.: PCT/JP99/00856

§ 371 Date: Aug. 28, 2000

§ 102(e) Date: Aug. 28, 2000

(87) PCT Pub. No.: WO99/43641

PCT Pub. Date: Sep. 2, 1999

(30) Foreign Application Priority Data

Feb. 27, 1998 (JP) ............................. 10-047120

(51) Int. Cl.$^7$ ..................... C07C 67/00; C07C 67/76; C07C 229/00; C07C 69/734
(52) U.S. Cl. ..................... 560/8; 560/1; 560/8; 560/45
(58) Field of Search .................................. 560/1, 8, 45

(56) References Cited

U.S. PATENT DOCUMENTS 5,334,740 A   8/1994   Takahashi et al.

FOREIGN PATENT DOCUMENTS

JP          10 251183        9/1998

OTHER PUBLICATIONS

Hatakeyama et al., "Convergent Synthesis of 1α.25–Dihydroxy–2β–(3–Hydroxypropoxy)Vitamin D$_3$", *Bioorganic Medicinal Chemistry Letters*, (1997), vol. 7, No. 22, pp. 2871–2874, Elsevier Science Ltd., Great Britain.

*Primary Examiner*—Sabiha Qazi
(74) *Attorney, Agent, or Firm*—Browdy and Neimark, P.L.L.C.

(57) ABSTRACT

The object of the present invention is to provide novel compounds corresponding to the A ring part of vitamin D derivatives having a substituent at the 2-position. According to the present invention, there are provided compounds of the general formula (1):

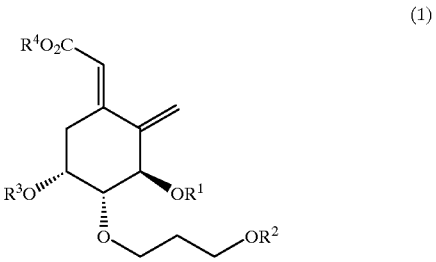

(wherein $R^1$, $R^2$ and $R^3$, which may be the same or different, represent a hydrogen atom or a protecting group and $R^4$ represents a lower alkyl group), intermediates for synthesizing them and a process for preparing them.

4 Claims, No Drawings

INTERMEDIATE COMPOUNDS IN THE SYNTHESIS OF THE A RING MOIETY OF 2-SUBSTITUTED VITAMIN D DERIVATIVES

This application is a 371 of PCT/JP99/00856, filed on Feb. 25, 1999.

TECHNICAL FIELD

The present invention relates to the A ring part of vitamin D derivatives, intermediates for synthesizing them and a process for preparing them.

More particularly, the present invention relates to the A ring part of vitamin D derivatives having a 3-hydroxypropyloxy group at the 2β-position, intermediates for synthesizing them and a process for preparing them.

BACKGROUND ART

Recently, some of the physiological activities of vitamins D have been revealed. It is known that a certain vitamin D, for example, 1α,25-dihydroxy vitamin $D_3$, exhibits a variety of physiological activities such as a calcium metabolism-controlling activity, proliferation-inhibiting and differentiation-inducing activities on cells such as tumor cells and an immune-controlling activity. However, 1α,25-dihydroxy vitamin $D_3$ disadvantageously causes hypercalcemia depending on the dose and/or the administration route and thus is not suitable for use as an antitumor agent, an anti-rheumatic agent, etc.

In order to isolate such activities of the vitamin D derivatives, numerous vitamin D derivatives have been synthesized recently and their physiological activities evaluated. For example, the synthesis of vitamin $D_3$ derivatives which have a substituent at the 2β-position is described in, for example, Japanese Patent Publication (Kokoku) No. 3-14303, Japanese Patent Publication (Kokai) No. 61-267549 and Japanese Patent Publication (Kokai) No. 6-41059. Some of those vitamin $D_3$ derivatives which have a substituent at the 2β-position exhibit calcium metabolism-controlling activity in vivo and differentiation-inducing activity on cells such as tumor cells and are known to be useful as a medicine, such as a therapeutic agent for diseases associated with abnormal calcium metabolism (e.g., osteoporosis, osteomalacia, etc.) and an antitumor agent. Among them, 2β-(3-hydroxypropoxy)-1α,25-dihydroxy vitamin $D_3$ is expected to be of practical use in treating osteoporosis, with a high blood level being able to be maintained for a long duration.

In synthesizing such vitamin D derivatives having a specific substituent at the 2-position, a process is known in which the A ring structure of a steroid compound, a starting material, is epoxylated and then cleaved so as to introduce the substituent to the 2-position (Japanese Patent Publication (Kokai) No. 61-267549; Chem. Pharm. Bull. 41(6), 1111–1113 (1993)). This process, however, has some disadvantages, such as difficulty in obtaining the raw material and low yield of the last step, i.e., light irradiation/thermal isomerization.

According to another known process for synthesizing the vitamin $D_3$ derivatives, the A ring part and the CD ring part of the vitamin D derivatives are synthesized separately and then coupled. Japanese Patent Publication (Kokai) No. 6-25039 discloses an A ring part of vitamin D derivatives and a process for synthesizing the A ring part. However, this process requires a considerably large number of reaction steps to synthesize the desired A ring part from a starting material. In addition, it is not suitable for synthesizing, for example, 2-(3-hydroxypropoxy)-1α,25-dihydroxy vitamin $D_3$, because a specific group cannot be introduced to the 2β-position by this process.

DISCLOSURE OF THE INVENTION

One object of the present invention is to provide compounds corresponding to the A ring part of vitamin D derivatives which have a substituent at the 2-position.

Another object of the present invention is to provide intermediates useful for the synthesis of the compounds of the present invention corresponding to the A ring part.

Still another object of the present invention is to provide a process for preparing the compounds of the present invention corresponding to the A ring part.

As a result of careful studies as to whether such vitamin derivatives that have a substituent at the 1-, 2- or 3-position stereochemically selectively can be synthesized by utilizing optically pure sugars, the inventors of the present invention have found that an A ring part having a substituent at a desired stereochemical conformation can be obtained by using D-mannitol as the starting material and thereby completed the present invention. Since D-mannitol is a low price sugar and readily available, the process of the present invention is expected to be applicable to the production of vitamin D derivatives on an industrial scale.

According to a first aspect of the present invention, there are provided compounds of the general formula (1):

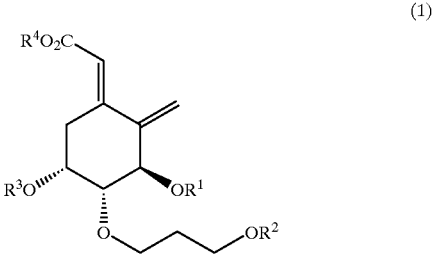

(1)

(wherein $R^1$, $R^2$ and $R^3$, which may be the same or different, represent a hydrogen atom or a protecting group and $R^4$ represents a lower alkyl group).

Preferably, $R^4$ in the general formula (1) is methyl.

According to a second aspect of the present invention, there are provided compounds of the general formula (2):

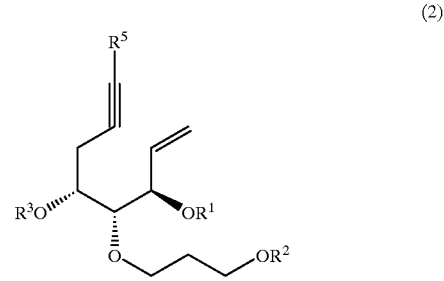

(2)

(wherein $R^1$, $R^2$ and $R^3$, which may be the same or different, represent a hydrogen atom or a protecting group; and $R^5$ represents a hydrogen atom or a lower alkoxycarbonyl group).

Preferably, $R^5$ in the general formula (2) is a methoxycarbonyl group.

According to a third aspect of the present invention, there are provided compounds of the general formula (3):

(3)

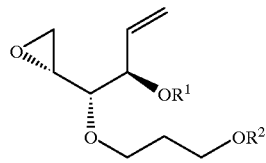

(wherein $R^1$ and $R^2$, which may be the same or different, represent a hydrogen atom or a protecting group).

The compounds of the general formulae (2) and (3) are intermediates for synthesizing the compounds of the general formula (1) of the present invention.

Japanese Patent Application No. 9-53316 (published as Japanese Patent Publication (Kokai) No. 10-251183 on Sep. 22, 1998 after the priority date of the present application) filed by the applicant of the present application discloses an epimer mixture of a compound having the same structure as the general formula (3) except for the stereochemical conformation. As is mentioned in the above, the present invention is aimed at synthesizing compounds corresponding to the A ring part of vitamin D derivatives, which are optically pure from the viewpoint of the positional and the stereochemical selectivity, without producing epimers by using an optically pure sugar, i.e. D-mannitol. However, the compounds of the general formulae (1) to (3) are novel and processes for synthesizing those compounds are not limited to a certain process. For example, the compounds of the general formula (3) of the present invention having a specific stereochemical conformation is theoretically obtainable by means of column chromatography, etc. from an epimer mixture of the compound disclosed in Japanese Patent Application No. 9-53316, that has the same structure as the compounds of the general formula (3) except for the stereochemical conformation. Compounds obtainable from such procedures are also included in the scope of the present invention. In addition, it is also possible to synthesize such vitamin D derivatives by coupling a compound corresponding to the CD ring part to a compound of the general formula (2) (wherein $R^5$ is H).

According to a fourth aspect of the present invention, there is provided a process for producing a compound of the general formula (1):

(1)

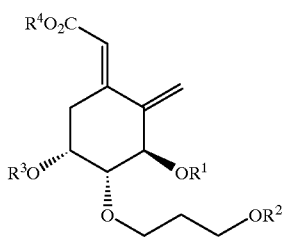

(wherein $R^1$, $R^2$ and $R^3$, which may be the same or different, represent a hydrogen atom or a protecting group and $R^4$ represents a lower alkyl group) comprising:

(a) reacting a compound of the general formula (3):

(3)

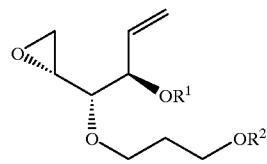

(wherein $R^1$ and $R^2$, which may be the same or different, represent a hydrogen atom or a protecting group) with a metal acetylide to obtain a compound of the general formula (2):

(2)

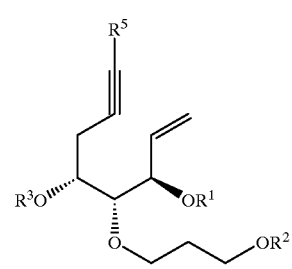

(wherein $R^1$, $R^2$ and $R^3$, which may be the same or different, represent a hydrogen atom or a protecting group; and $R^5$ represents a hydrogen atom);

(b) reacting the compound of the general formula (2) with a lower alkyl halogenated carbonate to obtain a compound of the general formula (2) (wherein $R^1$, $R^2$ and $R^3$, which may be the same or different, represent a hydrogen atom or a protecting group; and $R^5$ represents a lower alkoxycarbonyl group); and (c) subjecting the compound of the general formula (2) obtained in the step (b) to a reaction of ring formation.

BEST MODE FOR CARRYING OUT THE INVENTION

Detailed mode of the present invention and specific examples for carrying out the present invention will be explained below.

In the description of the present application, $R^1$, $R^2$ and $R^3$, which may be the same or different, represent a hydrogen atom or a protecting group. "Protecting group" refers a group protecting a hydroxy group and includes any protecting groups removable by conventional deprotecting means (e.g., hydrolysis, oxidative cleavage, reductive cleavage or hydrogenlysis) without substantially giving harmful effect to other portions of the molecule.

Examples of the protecting groups are as follows:

(I) an acyl group represented by $R^aCO$— (wherein $R^a$ is a hydrogen atom, a C1–C6 alkyl group, a C1–C6 haloalkyl group or a C6–C30 aryl group); for example, formyl, acetyl, propionyl, butyryl, isobutyryl, valeryl, isovaleryl, pivaloyl, caproyl, benzoyl, trifluoroacetyl, etc.;

(II) an alkoxycarbonyl group represented by $R^bOCO$— (wherein $R^b$ is a C1–C6 alkyl group, a C1–C6 alkenyl group, a C7–C9 aralkyl group, or a C6–C30 aryl group); for example, methoxycarbonyl, ethoxycarbonyl, propoxycarbonyl, isopropoxycarbonyl, allyloxycarbonyl, benzyloxycarbonyl, phenoxycarbonyl, etc.;

(III) a trisubstituted silyl group represented by the following formula:

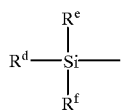

(wherein $R^d$, $R^e$ and $R^f$, which are the same or different, represent a C1–C6 alkyl group, a C6–C30 aryl group or a C7–C9 aralkyl group); for example, trimethylsilyl, triethylsilyl, triisopropylsilyl, t-butyldimethylsilyl, t-butyldiphenylsilyl, tribenzylsilyl, etc.;

(IV) an 1-alkoxy or 1-mercaptoalkyl group represented by the following formula:

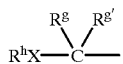

{wherein X represents an oxygen atom or a sulfur atom and $R^g$ and $R^{g'}$ each represent a hydrogen atom or a C1–C6 alkyl group; $R^h$ is a substituted or unsubstituted C1–C6 alkyl group [examples of the substituent are a lower alkoxy group, a halogen atom (e.g. chlorine), an alkyl substituted silyl group (e.g. trimethylsilyl group) and a phenyl group which may be substituted with an alkoxy group, a halogen atom, etc.]}; for example, methoxymethyl, methoxyethoxymethyl, 1-ethoxyethyl, methoxyisopropyl, methylthiomethyl, t-butylthiomethyl, β-trichloroethyloxymethyl, trimethylsilylethoxymethyl, p-methoxybenzyloxymethyl, p-chlorobenzyloxymethyl, etc.;

(V) an 2-oxacycloalkyl group represented by the following formula:

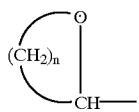

(wherein n is an integer of 3 to 6); for example, a tetrahydrofuranyl group, a tetrahydropyranyl group, etc.; and (VI) an aralkyl group such as a benzyl group.

In the general formula (1) of the present application, $R^4$ represents a lower alkyl group. The carbon number of the lower alkyl group is generally 1 to 6, preferably 1 or 2 and more preferably 1.

In the general formula (2) of the present application, $R^5$ represents a hydrogen atom or a lower alkoxycarbonyl group. The carbon number of the lower alkyl moiety of the lower alkoxycarbonyl group is generally 1 to 6, preferably 1 or 2 and more preferably 1. In other words, when $R^5$ is a lower alkoxycarbonyl group, $R^5$ is preferably a methoxycarbonyl group or an ethoxycarbonyl group.

Compounds of the general formula (1) of the present invention can be synthesized from a compound of the general formula (3) via a compound of the general formula (2); the synthesis process and the compounds of the general formulae (2) and (3) also form one aspect of the present invention, as is mentioned in the above.

Compounds of the general formula (3) of the present invention can be synthesized, for example, according to the following reaction scheme 1 using D-mannitol as a starting material.

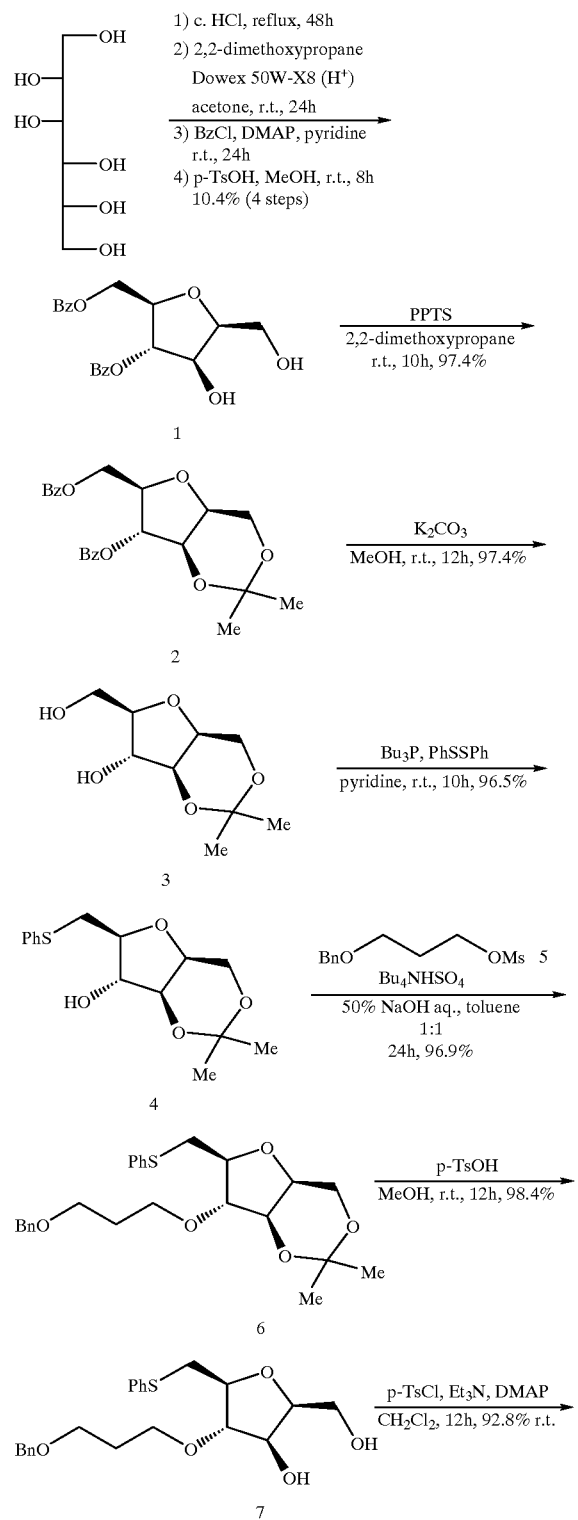

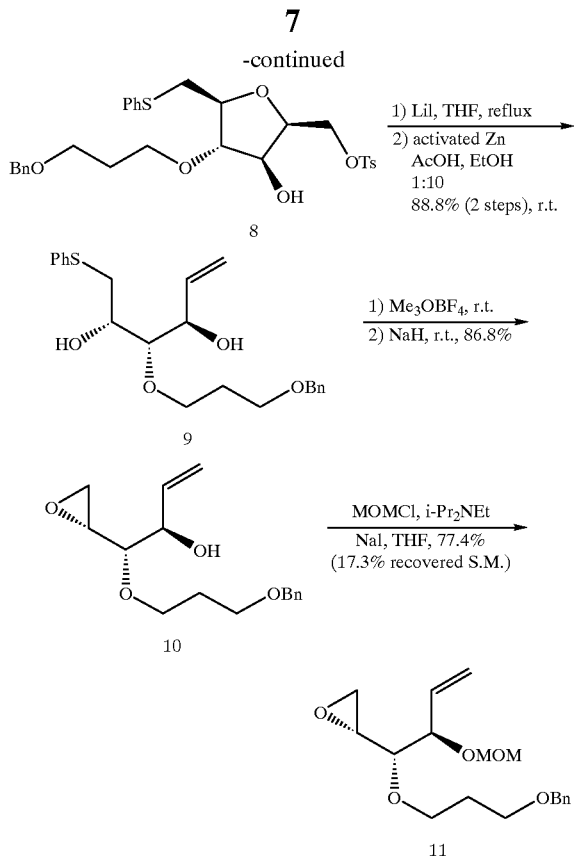

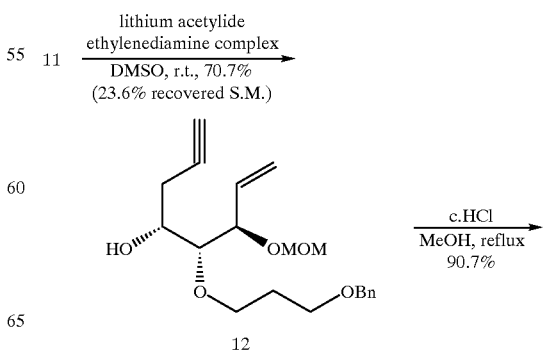

The compound 2 (2,5-anhydro-4,6-di-O-benzoyl-1,3-O-isopropylidene-D-glucitol) in the reaction scheme 1 is a known compound and is synthesizable from D-mannitol by the process described in, for example, Azeez M. Mubarak et al. J. C. S. Perkin I (1982), p.809–814 (the process shown in the above reaction scheme 1 is a modification of this process). In the following Examples of the present application, the compound 2 is used as the starting material. Acidic conditions of the process for forming a tetrahydrofuran ring from sugars such as D-mannitol is discussed by R. Barker in J.Org.Chem. (1970) Vol. 35, No. 2, p.461–464 and stereochemistry of the skeleton structure of the compound 2 is discussed by Theodore A. W. Koerner, Jr. et al. in Carbohydrate Research, (1977) 59, p.403–416. Both of these documents relate to a process for synthesizing compounds of the reaction scheme 1 from D-mannitol and the content of these documents is incorporated into this application by reference.

In the reaction scheme 1, the compound 4 is synthesized by selectively removing and changing the protecting groups of the compound 2. In the compound 4, only a hydroxy group that is to be at the 2-position of a vitamin D derivative when the compound 4 is synthesized as the A ring part of the vitamin D derivative is deprotected. By reacting such a compound with the compound 5 (3-benzyloxy-1-methanesulfonyloxypropane), a compound corresponding to the A ring part of vitamin D derivatives, which have a specific substituent at 2-position selectively in position and stereochemistry, can be synthesized.

3-Benzyloxy-1-methanesulfonyloxypropane refereed as the compound 5 in the reaction scheme 1 forms the 2-position substituent of the vitamin D derivatives and can be synthesized from a starting material such as 3-benzyloxypropanol (a known compound described by M. J. Martinelli, J. Org. Chem. 1990, 55, 5065–5073) by substituting the hydrogen atom of the hydroxy group, for example, according to a process described in Example 1.

The compound 4 is reacted with the compound 5 to give the compound 6 which is to be appropriately deprotected and protected to give the compound 8. Details of the process, conditions, etc. for deprotection and protection are known in this technical field and thus those skilled in the art can appropriately select such a process, conditions, etc.

The compound 8 can be obtained by appropriately deprotecting and protecting the compound 6 obtained by reacting the compound 4 with the compound 5. Details of the method, conditions, etc. for deprotection and protection are known in this technical field and those skilled in the art can appropriately select such a method, conditions, etc.

Then the compound 9 can be obtained by subjecting the compound 8 to a reaction of ring cleavage. The ring cleavage can be carried out by a 2-step reaction as shown in Example 7 to be described later: first, the compound 8 is reacted with an appropriate metallic halogenated compound, such as lithium iodide (LiI), sodium iodide, potassium iodide and cesium iodide, in the presence of an ether such as tetrahydrofuran (THF) or a hydrocarbon such as benzene, toluene and hexane; then reacted with activated zinc and the like in the presence of an appropriate solvent (e.g., a mixture of carboxylic acids such as acetic acid and alcohols such as ethanol or water). Alternatively, the ring cleavage can be proceeded by reacting the compound 8 with solely samarium iodide (II) (SmI$_2$) in the presence of a solvent such as ethers (e.g., tetrahydrofuran (THF)), alcohols (e.g., ethanol), water and the like.

Then, the compound 10 is obtained by epoxylating the terminal moiety of the compound 9; the compound 11 is obtained by protecting the hydroxy group of the compound 10. The compounds 10 and 11 are novel and both of them have a basic skeleton represented by the general formula (3).

The compound 11 is an intermediate for synthesizing the compounds of the present invention having the general formula (1); the following reaction scheme 2 shows an example process for synthesizing the compound 16 from the compound 11. The compound 16 is included in the compounds of the present invention having the general formula (1).

Reaction Scheme 2

9

-continued

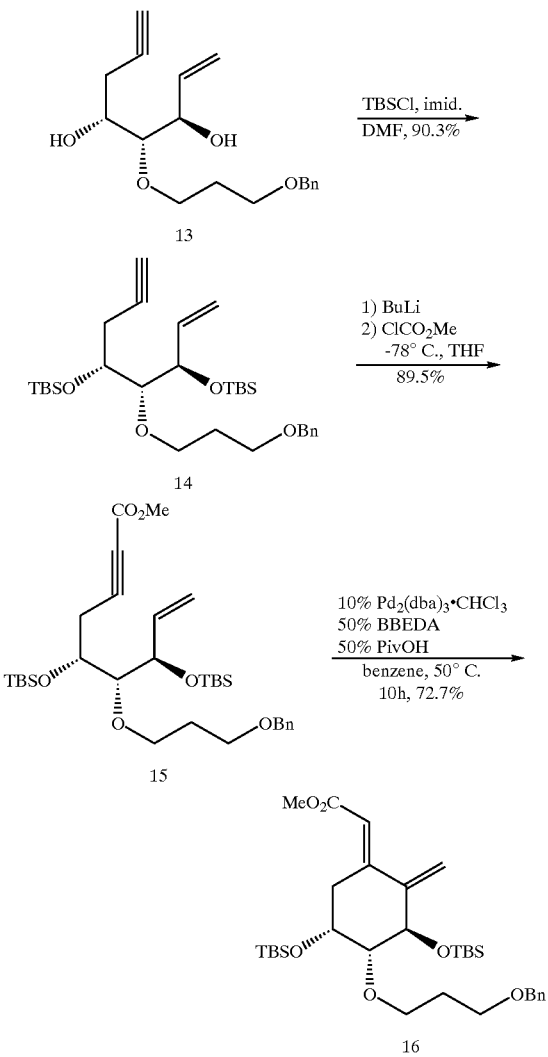

10 ring part of vitamin D derivatives. Although a specific example of the ring formation is shown in Example 14, it is apparent that the ring formation can be carried out under other preferred conditions. In general, the ring formation can be carried out by reacting compound 15 in an appropriate solvent (e.g., benzene, toluene, tetrahydrofuran, N,N-dimethylformamide, acetonitrile, hexane, etc.) at a temperature ranging from 20° C. to 80° C., preferably from 30° C. to 60° C. in the presence of 0 valent palladium (e.g., tetra(triphenylphosphine)palladium (0), tris(dibenzylidene acetone)(chloroform)dipalladium (0), etc.) or divalent palladium (e.g., palladium acetate (II), dichlorobis (triphenylphosphine)palladium (II), etc.) and a preferable ligand (e.g., triphenylphosphine, tris(o-tolyl)phosphine, tirmethylphosphite, 1,2-bis(diphenyl-phosphino)ethane, 1,3-bis(diphenylphosphino)propane, 1,4-bis (diphenylphosphino)butane, 1,1'-bis(diphenyl-phosphino) ferrocene, N,N'-bis(benzylidene)ethylenediamine (BBEDA), etc.) and a preferable addition product (e.g., acetic acid, pivalic acid, hydroquinone, ammonium formate, etc.).

The present invention will be further illustrated in detail by the following Examples, however the present invention is not limited by the following Example.

First, for obtaining the compound 12, the compound 11 is subjected to reaction with a metallic acetylide such as lithium acetylide, sodium acetylide and potassium acetylide (preferably such a metallic acetylide is used in a complex form with ethylenediamine and the like) in an appropriate solvent such as DMSO at −10° C.~20° C., preferably at 0° C.~1020 C., or with a metallic acetylide such as lithium acetylide, sodium acetylide and potassium acetylide in an appropriate solvent such as an ether (e.g., THF) or a hydrocarbon (e.g., benzene, toluene and hexane) in the presence of a Lewis acid such as boron trifluoride.diethyl ether, etc. Then, the compound 14 is obtained by appropriately removing or adding protecting groups. The compound 15 can be obtained as follows: after subjecting compound 14 to reaction with a metallic alkyl (e.g., n-butyl lithium, s-butyl lithium, etc.) or a metallic alkyl halogenated compound (e.g., methyl magnesium iodide, ethyl magnesium bromide, etc.), the terminal moiety of the resulting compound is alkoxycarbonylated by reaction with a halogenated carbonic acid ester (e.g., methyl chlorocarbonate (ClCO$_2$CH$_3$), ethyl chlorocarbonate, etc.) in the presence of a preferred solvent (e.g., THF, diethyl ether, etc.), generally at a temperature ranging from −100° C. to −50° C., preferably from −100° C. to −70° C.

Finally, the compound 15 is subjected to a reaction of ring formation to give the compound 16 corresponding to the A

EXAMPLES

Example 1

Synthesis of 3-benzyloxy-1-methanesulfonyloxypropane

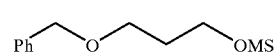

5

Under cooling with ice, MsCl (1.69 ml, 21.80 mmol), triethylamine (3.80 ml, 27.26 mmol) and DMAP (30 mg) were added to a solution of 3-benzyloxypropanol (3.021 g, 18.12 mmol) in CH$_2$Cl$_2$ (50 ml) in that order, followed by stirring for 12 hours at room temperature. The mixture was diluted with CHCl$_3$; the organic layer was washed with H$_2$O and brine successively and dried over MgSO$_4$. The resultant was distilled for removing the solvent under reduced pressure and the thus obtained residue was subjected to silica gel column chromatography (100 g) using ethyl acetate/hexane (1:3 v/v) as an eluent to give the titled compound 5 (4.412 g, 99.7%) as a colorless oil.

IRvmax(neat) 1353 cm$^{-1}$.

$^1$H-NMR (300 MHz, CDCl$_3$) δ: 7.43–7.26(m, 5H), 4.51(s, 2H), 4.36(t, 2H, J=6.2 Hz), 3.59(t, 2H, J=5.9 Hz), 2.96(s, 3H), 2.04(quint, 2H, J=6.0 Hz).

MS m/z: 91(100%), 244(M$^+$).

HRMS Calcd. for C$_{11}$H$_{16}$O$_4$S(M$^+$):244.0770, Found 244.0785.

Example 2

Synthesis of 2,5-anhydro-1,3-O-isopropylidene-D-glucitol

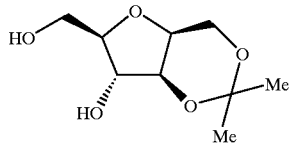

3

To a solution of 2,5-anhydro-4,6-di-O-benzoyl-1,3-O-isopropylidene-D-glucitol (6.187 g, 15.0 mmol) in methanol (150 ml), $K_2CO_3$ (5.252 g, 38.0 mmol) was added and stirred for 12 hours at room temperature. The mixture was distilled for removing the solvent under reduced pressure and the resultant was diluted with ether and then filtered through Celite. The resultant was distilled for removing the solvent under reduced pressure and the thus obtained crude product was subjected to silica gel column chromatography (50 g) using ethyl acetate as an eluent to give the titled compound 3 (2.985 g, 97.4%). A portion of the compound was recrystallized from ether/hexane to give colorless prismatic crystals.

mp 94–95°,
$[\alpha]_D^{28}$+28.39 (c=1.05, $CHCl_3$).
IRvmax(nujol) 3366 $cm^{-1}$.
$^1$H-NMR (300 MHz, $CDCl_3$) δ: 4.21–3.91(m, 6H), 3.84–3.78(m, 2H), 3.03–2.97 (m, 2H, $D_2O$ exchangeable), 1.45(s, 3H), 1.38(s, 3H).
MS m/z:59 (100%), 189($M^+$–15).
HRMS Calcd. for $C_8H_{13}O_5(M^+$–15) 189.0763, Found 189.0771.
Elemental analysis Calcd. for $C_9H_{16}O_5$: C, 52.93; H, 7.90. Found C, 53.03; H, 7.95.

Example 3

Synthesis of 2,5-anhydro-6-deoxy-1,3-O-isopropylidene-6-phenylthio-D-glucitol

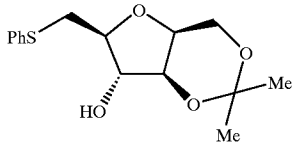

4

Under cooling with ice, diphenyldisulfide (629 mg, 2.88 mmol) and tributylphosphine (957 μl, 3.84 mmol) were added in that order to a solution of the compound 3 (392 mg, 1.92 mmol) of Example 2 in pyridine (20 ml) and stirred for 10 hours at room temperature. The mixture was distilled for removing the solvent under reduced pressure and the thus obtained residue was subjected to silica gel column chromatography (10 g) using ethyl acetate/hexane (1:1 v/v) as an eluent to give the titled compound 4 (549 mg, 96.5%). A portion of the compound was recrystallized from ether/hexane to give colorless needle-like crystals.

mp 107–108°,
$[\alpha]_D^{26}$–28.27 (c=2.36, $CHCl_3$).
IRvmax (nujol) 3490 $cm^{-1}$.
$^1$H-NMR (300 MHz, $CDCl_3$) δ: 7.43–7.36(m, 2H), 7.33–7.24(m, 2H), 7.22–7.15(m, 1H), 4.22–4.14(m, 2H), 4.11–3.89(m, 4H), 3.34(dd, 1H, J=13.7, 5.5 Hz), 3.17(dd, 1H, J=13.5, 9.3 Hz), 2.12(d, 1H, J=3.8 Hz, $D_2O$ exchangeable), 1.42(s, 3H), 1.39(s, 3H).

MS m/z:59(100%), 296($M^+$).

HRMS Calcd. for $C_{15}H_{16}O_4S$ ($M^+$) 296.1083, Found 296.1083.

Elemental analysis Calcd. for $C_{15}H_{20}O_4S$: C, 60.79; H, 6.80; S, 10.82. Found C, 60.75; H, 6.78; S, 10.81.

Example 4

Synthesis of 2,5-anhydro-4-O-(3-benzyloxypropyl)-6-deoxy-1,3-O-isopropylidene-6-phenylthio-D-glucitol

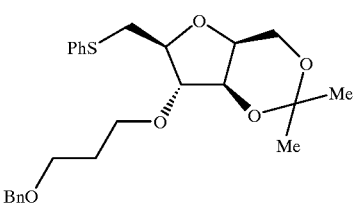

6

Under cooling with ice, a 50% aqueous NaOH solution (4 ml), the compound 5 (562 mg, 2.30 mmol) of Example 1 and tetrabutyl ammonium hydrogensulfite (260 mg, 766 μmol) were added in that order to a solution of the compound 4 (227 mg, 766 μmol) of Example 3 in toluene (4 ml) and vigorously stirred for 24 hours at room temperature. The mixture was extracted with ether; the organic layer was washed with $H_2O$ and brine successively and dried over $MgSO_4$. The resultant was distilled for removing the solvent under reduced pressure and the thus obtained residue was subjected to silica gel column chromatography (10 g) using ethyl acetate/hexane (1:6 v/v) as an eluent to give the titled compound 6 (330 mg, 96.9%) as a colorless oil.

$[\alpha]_D^{27}$–19.10 (c=1.02, $CHCl_3$).

IRvmax (neat) 3060, 3030 $cm^{-1}$;

$^1$H-NMR (300 MHz, $CDCl_3$) δ: 7.41–7.12(m, 10H), 4.48 (dd, 2H, J=14.0, 11.8 Hz), 4.19(d, 1H, J=2.7 Hz), 4.08–3.93 (m, 3H), 3.83–3.78(m, 2H), 3.62–3.45(m, 4H), 3.33(dd, 1H, J=13.6, 5.4 Hz), 3.17(dd, 1H, J=13.7, 9.3 Hz), 1.84(quint, 2H, J=6.2 Hz), 1.41(s, 3H), 1.39(s, 3H).

$^{13}$C-NMR (75 MHz, $CDCl_3$) δ: 138.3(s), 135.8(s), 128.75 (d), 128.69(d), 128.1(d), 127.31(d), 127.28(d), 125.7(d), 97.0(s), 87.2(d), 82.8(d), 73.5(d), 72.8(d), 72.5(t), 66.5(t), 66.0(t), 60.1(t), 35.7(t), 29.6(t), 28.6(q), 18.5(q).

MS m/z:91(100%), 444($M^+$).

HRMS Calcd. for $C_{25}H_{32}O_5S(M^+$) 444.1971, Found 444.1948.

Example 5

Synthesis of 2,5-anhydro-4-O-(3-benzyloxypropyl)-6-deoxy-6-phenylthio-D-glucitol

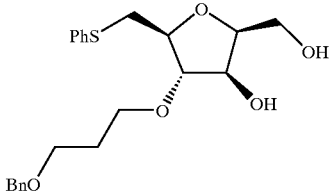

p-TsOH (10 mg) was added to a solution in methanol (20 ml) of the compound 6 (894 mg, 2.10 mmol) obtained in Example 4 and stirred for 12 hours at room temperature. The mixture was distilled for removing the solvent under reduced pressure and the thus obtained crude product was subjected to silica gel column chromatography (20 g) using ethyl acetate/hexane (1:1 v/v) as an eluent to give the titled compound 7 (800 mg, 98.4%) as a colorless oil.

$[\alpha]_D^{27}$+8.76(c=1.01, CHCl$_3$).

IRvmax(neat) 3406 cm$^{-1}$.

$^1$H-NMR (300 MHz, CDCl$_3$) δ: 7.41–7.14(m, 10H), 4.48 (s, 2H), 4.23(br s, 1H), 4.03–3.84(m, 4H), 3.77–3.61(m, 3H), 3.59–3.45(m, 3H), 3.25(d, 2H, J=5.8 Hz), 2.55(br s, 1H, D$_2$O exchangeable), 1.84(quint, 2H, J=6.2 Hz).

$^{13}$C-NMR(75 MHz, CDCl$_3$) δ: 138.2(s), 135.7(s), 129.2 (d), 128.9(d), 128.3(d), 127.6(d), 127.5(d), 126.2(d), 88.5 (d), 81.7(d), 80.1(d), 76.9(d), 72.8(t), 66.8(t), 66.5(t), 61.1 (t), 36.5(t), 29.7(t).

MS m/z:91(100%), 404(M$^+$).

HRMS Calcd. for C$_{22}$H$_{28}$O$_5$S(M$^+$) 404.1658, Found 404.1650.

Example 6

Synthesis of 2,5-anhydro-4-O-(3-benzyloxypropyl)-6-deoxy-6-phenylthio-1-O-(p-toluenesulfonyl)-D-glucitol

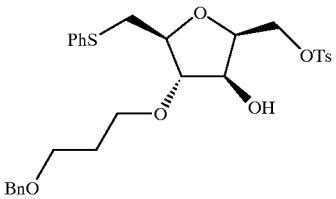

Under cooling with ice, p-TsCl (70 mg, 366 μmol), triethylamine (107 μl, 768 μmol) and DMAP (2 mg) were added in that order to a solution in CH$_2$Cl$_2$ (5 ml) of the compound 7 (141 mg, 349 μmol) obtained in Example 5 and stirred for 12 hours at room temperature. The mixture was diluted with CHCl$_3$; the organic layer was washed with H$_2$O and brine successively and dried over MgSO$_4$. The resultant was distilled for removing the solvent under reduced pressure and the thus obtained residue was subjected to silica gel column chromatography (20 g) using ethyl acetate/hexane (1:4 v/v) as an eluent to give the titled compound 8 (181 mg, 92.8%) as a colorless oil.

$[\alpha]_D^{26}$+0.99(c=1.14, CHCl$_3$).

IRvmax(neat) 3522, 1362 cm$^{-1}$.

$^1$H-NMR (300 MHz, CDCl$_3$) δ: 7.79(d, 2H, J=8.2 Hz), 7.38–7.13(m, 12H), 4.47(s, 2H), 4.30(dd, 1H, J=12.4, 8.2 Hz), 4.15–4.05(m, 3H), 3.96(dt, 1H, J=6.0, 2.5 Hz), 3.71(d, 1H, J=2.5 Hz), 3.63–3.46(m, 4H), 3.13(d, 2H, J=5.8 Hz), 2.68(d, 1H, J=6.6 Hz, D$_2$O exchangeable), 2.43(s, 3H), 1.82(quint, 2H, J=6.2 Hz).

$^{13}$C-NMR(75 MHz, CDCl$_3$) δ: 145.0(s), 138.2(s), 135.5 (s), 132.4(s), 129.8(d), 129.2(d), 128.9(d), 128.3(d), 127.9 (d), 127.6(d), 127.5(d), 126.2(d), 88.0(d), 82.7(d), 78.8(d), 74.6(d), 72.7(t), 67.9(t), 66.7(t), 66.3(t), 36.2(t), 29.7(t), 21.3(q),.

MS m/z:91 (100%), 558(M$^+$).

HRMS Calcd. for C$_{29}$H$_{34}$O$_7$S$_2$(M$^+$) 558.1746, Found 558.1731.

Example 7

Synthesis of 4(S)-(3-benzyloxypropyloxy)-3(R),5 (S)-dihydroxy-6-phenylthio-1-hexene

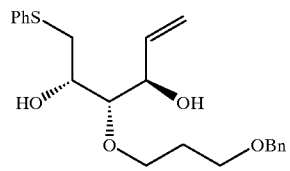

Lithium iodide (1.253 g, 9.36 mmol) was added to a solution in THF (20 ml) of the compound 8 (523 mg, 936 μmol) obtained in Example 6, followed by heating under reflux for 10 hours. The mixture was distilled for removing the solvent under reduced pressure and diluted with ether; the organic layer was washed with H$_2$O and brine successively and dried over MgSO$_4$. The resultant was distilled for removing the solvent under reduced pressure and the thus obtained product was subjected to the next reaction without further purification. The product was dissolved in a mixture of ethanol (15 ml) and acetic acid (1.5 ml) and mixed with activated zinc (1.222 g, 18.7 mmol), followed by stirring for 8 hours at room temperature. The reaction solution was filtered through Celite and distilled for removing the solvent under reduced pressure; then the organic layer was diluted with ether, washed with H$_2$O and a saturated aqueous NaHCO$_3$ solution successively and dried over MgSO$_4$. The resultant was distilled for removing the solvent under reduced pressure and the thus obtained residue was subjected to silica gel column chromatography (20 g) using ethyl acetate/hexane (1:4 v/v) as an eluent to give the titled compound 9 (323 mg, 88.8%) as a colorless oil.

$[\alpha]_D^{23}$+44.15 (c=1.01, CHCl$_3$).

IRvmax(neat) 3430 cm$^{-1}$.

$^1$H-NMR(300 MHz, CDCl$_3$) δ: 7.40–7.16(m, 10H), 5.91 (ddd, 1H, J=17.3, 10.6, 5.4 Hz), 5.31(dt, 1H, J=17.0, 1.4 Hz), 5.17(dt, 1H, J=10.4, 1.4 Hz), 4.49(s, 2H), 4.34–4.24(m, 1H), 3.87–3.77(m, 1H), 3.77–3.64(m, 2H), 3.54(t, 2H, J=6.2 Hz), 3.39–3.30(m, 2H), 3.04–2.92(m, 3H), 1.85(quint, 2H, J=6.2 Hz).

$^{13}$C-NMR (75 MHz, CDCl$_3$) δ: 138.0(s), 137.5(d), 135.9 (s), 128.8(d), 128.7(d), 128.1(d), 127.4(d), 127.3(d), 125.8 (d), 115.5(t), 82.6(d), 72.5(t), 71.3(d), 69.6(d), 68.9(t), 66.7 (d), 72.7(t), 37.8(t), 29.8(t).

MS m/z:91 (100%), 331(M+−57).

HRMS Calcd. for $C_{19}H_{23}O_3S$ (M+−57) 331.1368, Found 331.1366.

Example 8

Synthesis of 3(S)-(3-benzyloxypropyloxy)-1,2(S)-epoxy-4(R)-hydroxy-5-hexene

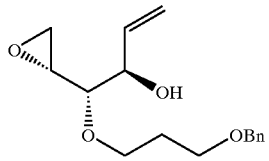

10

Under cooling with ice, trimethyloxonium tetrafluoroborate (119 mg, 803 μmol) was added to a solution in $CH_2Cl_2$ (20 ml) of the compound 9 (309 mg, 795 μmol) obtained in Example 7. The mixture was returned to room temperature, stirred for 3 hours and then mixed with NaH (60% in oil, 70 mg, 1.749 mmol) under cooling with ice; the mixture was returned to room temperature and then stirred for 9 hours. The resultant was diluted with $CHCl_3$ and then under cooling with ice mixed with a saturated aqueous solution of ammonium chloride; the organic layer was washed with $H_2O$ and brine successively and dried over $MgSO_4$. The resultant was distilled for removing the solvent under reduced pressure and the thus obtained residue was subjected to silica gel column chromatography (20 g) using ethyl acetate/hexane (1:4 v/v) as the eluent to give the titled compound 10 (192 mg, 86.8%) as a colorless oil.

$[\alpha]_D^{29}$+10.74(c=1.06, $CHCl_3$).

IRvmax(neat) 3446 $cm^{-1}$.

$^1$H-NMR (300 MHz, $CDCl_3$) δ: 7.39–7.26(m, 5H), 5.94 (ddd, 1H, J=17.2, 10.5, 6.0 Hz), 5.40(dt, 1H, J=17.3, 1.6 Hz), 5.25(dt, 1H, J=10.7, 1.4 Hz), 4.51(s, 2H), 4.20–4.12(m, 1H), 3.82(dt, 1H, J=9.3, 6.0 Hz), 3.62–3.49(m, 3H), 3.11(t, 1H, J=5.4 Hz), 3.03–3.00(m, 1H), 2.83–2.75(m, 3H), 1.86 (quint, 2H, J=6.1 Hz).

$^{13}$C-NMR(75 MHz, $CDCl_3$) δ138.2(s), 136.9(d), 128.3 (d), 127.6(d), 127.5(d), 116.5(t), 81.3(d), 73.3(d), 72.8(t), 68.7(t), 66.9(t), 50.6(d), 44.8(t), 29.9(t).

MS m/z:91 (100%), 221(M+−57).

HRMS Calcd. for $C_{13}H_{17}O_3$ (M+−57) 221.1178, Found 221.1183.

Example 9

Synthesis of 3(R)-(3-benzyloxypropyloxy)-1,2(S)-epoxy-4(R)-methoxymethyloxy-5-hexene

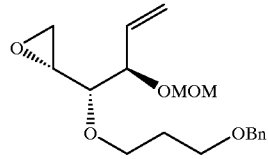

11

Under cooling with ice, methoxymethyl chloride (460 μl, 6.05 mmol), i-$Pr_2$NEt (di(isopropyl)ethylamine) (2.11 ml, 12.10 mmol) and NaI (30 mg) were added to a solution in THF (20 ml) of the compound 10 (347 mg, 1.25 mmol) obtained in Example 8; the mixture was returned to room temperature and stirred for 90 hours. Under cooling with ice, the mixture was diluted with ether and mixed with $H_2O$; the organic layer was washed with $H_2O$ and brine successively and dried over $MgSO_4$. The resultant was distilled for removing the solvent under reduced pressure and the thus obtained residue was subjected to silica gel column chromatography (20 g) using ethyl acetate/hexane (1:6 v/v) as an eluent to give the titled compound 11 (312 mg, 77.4%) as a colorless oil. The compound 10 (60 mg, 17.3%) used as the starting material was also recovered.

$[\alpha]_D^{26}$31 51.26(C=1.21, $CHCl_3$).

IRvmax(neat) 3062 $cm^{-1}$.

$^1$H-NMR (300 MHz, $CDCl_3$) δ: 7.38–7.24(m, 5H), 5.86 (ddd, 1H, J=17.5, 10.2, 7.5 Hz), 5.38–5.25(m, 2H), 4.73(d, 1H, J=6.6 Hz), 4.62(d, 1H, J=6.6 Hz), 4.49(s, 2H), 4.23(dd, 1H, J=7.7, 3.8 Hz), 3.74(dt, 1H, J=9.3, 6.2 Hz), 3.65–3.51 (m, 3H), 3.39(s, 3H), 3.20(dd, 1H, J=5.2, 3.8 Hz), 3.16–3.10 (m, 1H), 2.84–2.76(m, 2H), 1.94–1.83(m, 2H).

$^{13}$C-NMR (75 MHz, $CDCl_3$) δ138.4(s), 134.3(d), 128.2 (d), 127.4(d), 127.3(d), 118.7(t), 93.7(t), 80.9(d), 77.0(d), 72.7(t), 68.5(t), 66.8(t), 55.2(q), 50.4(d), 45.2(t), 30.0(t).

MS m/z:91 (100%), 277 (M+−45).

HRMS Calcd. for $C_{16}H_{21}O_4$(M+−45) 277.1440, Found 277.1425

Example 10

Synthesis of 4(R)-(3-benzyloxypropyloxy)-5(R) hydroxy-3(R)-methoxymethyloxy-1-octen-7-ine

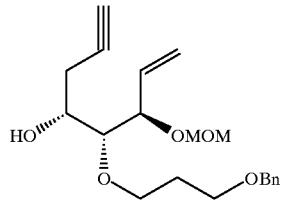

12

Under cooling with ice, lithium acetylide/ethylenediamine complex (109 mg, 1.18 mmol) was added to a solution in DMSO (5 ml) of the compound 11 (127 mg, 394 μmol) obtained in Example 9; the mixture was returned to room temperature and stirred for 48 hours. Under cooling with ice, the mixture was diluted with ether and mixed with a saturated aqueous solution of ammonium chloride; the organic layer was washed with $H_2O$ and brine successively and dried over $MgSO_4$. The resultant was distilled for removing the solvent under reduced pressure and the thus obtained residue was subjected to silica gel column chromatography (20 g) using ethyl acetate/hexane (1:6 v/v) as an eluent to give the titled compound 12 (97 mg, 70.7%) as a colorless oil. The compound 11 (30 mg, 23.6%) used as the starting material was also recovered.

$[\alpha]_D^{30}$-23.61(C=1.04, $CHCl_3$).

IRvmax (neat) 3464, 3294, 2116 $cm^{-1}$.

$^1$H-NMR (300 MHz, $CDCl_3$) δ: 7.39–7.25(m, 5H), 5.89 (ddd, 1H, J=17.4, 10.4, 7.1 Hz), 5.40–5.26(m, 2H), 4.68(d, 1H, J=6.6 Hz), 4.63(d, 1H, J=6.6 Hz), 4.50(s, 2H), 4.39(dd, 1H, J=7.0, 3.4 Hz), 3.97–3.87(m, 1H), 3.82–3.64(m, 2H), 3.60–3.52(m, 2H), 3.44–3.38(m, 4H), 3.20(d, 1H, J=4.9 Hz, $D_2O$ exchangeable), 2.64–2.46(m, 2H), 2.05(t, 1H, J=2.6 Hz), 1.88(quint, 2H, J=6.2 Hz).

MS m/z:91(100%), 317($M^+$-31).

HRMS Calcd. for $C_{19}H_{25}O_4$($M^+$-31) 317.1753, Found 317.1760.

Example 11

Synthesis of 4(R)-(3-benzyloxypropyloxy)-3(R),5(R)-dihydroxy-1-octen-7-ine

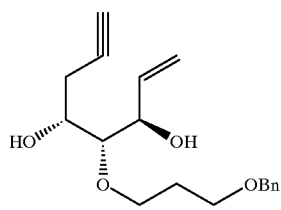

13

One droplet of concentrated hydrochloric acid was added to a solution in methanol (5 ml) of the compound 12 (57 mg, 164 μmol) obtained in Example 10, followed by heating under reflux for 30 min. The reaction solution was allowed to stand for cooling, distilled for removing the solvent under reduced pressure and diluted with ether; the organic layer was washed with water, a saturated aqueous solution of $NaHCO_3$ and brine successively and dried over $MgSO_4$. The resultant was distilled for removing the solvent under reduced pressure and the thus obtained residue was subjected to silica gel column chromatography (10 g) using ethyl acetate/hexane (1:3 v/v) as an eluent to give the titled compound 13 (45 mg, 90.7%) as a colorless oil.

$[\alpha]_D^{30}$+48.78(C=0.98, $CHCl_3$).

IRvmax (neat) 3416, 3302, 2116 $cm^{-1}$.

$^1$H-NMR (300 MHz, $CDCl_3$) δ: 7.39–7.25(m, 5H), 5.99 (ddd, 1H, J=17.2, 10.6, 5.2 Hz), 5.38(dt, 1H, J=17.3, 1.6 Hz), 5.23(dt, 1H, J=10.4, 1.6 Hz), 4.51(s, 2H), 4.37(br s, 1H), 3.94–3.85(m, 1H), 3.73(t, 2H, J=6.2 Hz), 3.55(t, 2H, J=6.0 Hz), 3.35(dd, 1H, J=7.1, 3.3 Hz), 2.89(br d, 1H, J=7.7 Hz, $D_2O$ exchangeable), 2.72(br d, 1H, J=4.9 Hz, $D_2O$ exchangeable), 2.62–2.44(m, 2H), 2.07(t, 1H, J=2.6 Hz), 1.86(quint, 2H, J=6.1 Hz).

MS m/z:91(100%), 247 ($M^+$-57).

HRMS Calcd. for $C_{15}H_{19}O_3$ ($M^+$-57) 247.1334, Found 247.1321.

Example 12

Synthesis of 4(R)-(3-benzyloxypropyloxy)-3(R),5(R)-bis(t-butyldimethylsilyloxy)-1-octen-7-ine

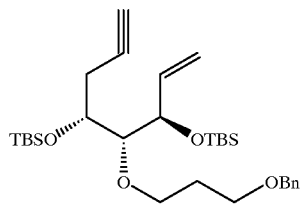

14

Imidazole (95 mg, 1.40 mmol) and t-butyldimethylsilyl chloride (105 mg, 699 μmol) were added to a solution in DMF (5 ml) of the compound 13 (71 mg, 233 μmol) obtained in Example 11 and stirred for 15 hours at room temperature. The reaction solution was diluted with ether; the organic layer was washed with $H_2O$ and brine successively and dried over $MgSO_4$. The resultant was distilled for removing the solvent under reduced pressure and the thus obtained residue was subjected to silica gel column chromatography (10 g) using ethyl acetate/hexane (1:50 v/v) as an eluent to give the titled compound 14 (45 mg, 90.3%) as a colorless oil.

$[\alpha]_D^{30}$+18.41(C=1.76, $CHCl_3$).

IRvmax (neat) 3312, 2120 $cm^{-1}$.

$^1$H-NMR (300 MHz, $CDCl_3$) δ: 7.35–7.25(m, 5H), 5.89 (ddd, 1H, J=17.2, 10.6, 6.5 Hz), 5.25(dt, 1H, J=17.3, 1.5 Hz), 5.14(dt, 1H, J=10.4, 1.5 Hz), 4.50(s, 2H), 4.18(t, 1H, J=6.5 Hz), 3.98(ddd, 1H, J=7.1, 5.0, 2.0 Hz), 3.85–3.66(m, 2H), 3.64–3.51(m, 2H), 3.28(dd, 1H, J=6.7, 1.8 Hz), 2.51–2.31(m, 2H), 1.95–1.80(m, 3H), 0.92–0.87(m, 18H), 0.10(s, 3H), 0.08(s, 3H), 0.06(s, 3H), 0.03(s, 3H).

MS m/z:91(100%), 475($M^+$-57).

HRMS Calcd. for $C_{26}H_{43}O_4Si_2$($M^+$-57) 475.2700, Found 475.2719.

Example 13

Synthesis of 4(R)-(3-benzyloxypropyloxy)-3(R),5(R)-bis(t-butyldimethylsilyloxy)-8-methoxycarbonyl-1-octen-7-ine

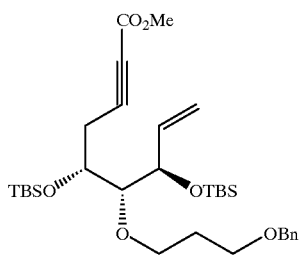

15

A solution in THF (5 ml) of the compound 14 (111 mg, 208 μmol) obtained in Example 12 was cooled to −78° C., mixed with n-BuLi (at 1.56M in hexane, 223 μl, 312 μmol), stirred for 1 hour at the same temperature and then mixed with methyl chlorocarbonate (32 μl, 416 μmol), followed by stirring for 3 hours. The mixture was diluted with ether, mixed with a saturated aqueous solution of NH$_4$Cl and returned to room temperature; the organic layer was washed with H$_2$O and brine successively and dried over MgSO$_4$. The resultant was distilled for removing the solvent under reduced pressure and the thus obtained residue was subjected to silica gel column chromatography (10 g) using ethyl acetate/hexane (1:40 v/v) as an eluent to give the titled compound 15 (110 mg, 89.5%) as a colorless oil.

$[\alpha]_D^{29}$+29.83(C=1.05, CHCl$_3$).

IRvmax (neat) 2238, 1718 cm$^{-1}$.

$^1$H-NMR (300 MHz, CDCl$_3$) δ: 7.38–7.24(m, 5H), 5.85 (ddd, 1H, J=17.0, 10.6, 6.2 Hz), 5.25(dt, 1H, J=17.0, 1.5 Hz), 5.15(dt, 1H, J=10.7, 1.5 Hz), 4.50(s, 2H), 4.15(br t, 1H, J=6.3 Hz), 4.04(ddd, 1H, J=7.0, 5.2, 1.6 Hz), 3.89–3.66(m, 5H), 3.64–3.49(m, 2H), 3.31(dd, 1H, J=6.5, 1.5 Hz), 2.63–2.47(m, 2H), 1.88(quint, 2H, J=6.4 Hz), 0.90(s, 9H), 0.89(s, 9H), 0.12(s, 3H), 0.08(s, 3H), 0.06(s, 3H), 0.03(s, 3H).

MS m/z:91 (100%), 533(M$^+$−57).

HRMS Calcd. for C$_{28}$H$_{45}$O$_6$Si$_2$ (M$^+$−57) 533.2754, Found 533.2736.

Example 14

Synthesis of 2(R)-(3-benzyloxypropyloxy)-1(R),3(R)-bis(t-butyldimethylsilyloxy)-5(E)-methoxycarbonylmethylene-6-methylenecyclohexane

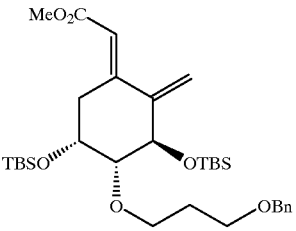

16

To a solution in benzene (3 ml) of the compound 15 (55 mg, 93 μmol) obtained in Example 13, Pd$_2$(dba)$_3$.CHCl$_3$ (9.6 mg, 9.3 μmol), BBEDA (11 mg, 47 μmol) and PivOH (at 0.1M on benzene, 470 μmol, 47 μmol) were added and stirred for 10 hours at 50° C. The reaction solution was allowed to stand for cooling and diluted with ether; the organic layer was washed with water and brine successively and dried over MgSO$_4$. The resultant was distilled for removing the solvent under reduced pressure and the thus obtained residue was subjected to silica gel column chromatography (10 g) using ether/hexane (1:20 v/v) as an eluent to give the titled compound 16 (40 mg, 72.7%) as a colorless oil.

$[\alpha]_D^{31}$−16.25(C=1.09, CHCl$_3$).

IRvmax (neat) 1718, 1641 cm$^{-1}$.

$^1$H-NMR (300 MHz, CDCl$_3$) δ: 7.34–7.25(m, 5H), 5.91(s, 1H), 5.17(s, 1H), 5.13(s, 1H), 4.49(s, 2H), 4.41(d, 1H, J=7.4 Hz), 4.27–4.20(m, 1H), 3.80–3.61(m, 5H), 3.56(t, 2H, J=6.5 Hz), 3.39(dd, 1H, J=14.7, 6.2 Hz), 3.22(dd, 1H, J=7.6, 2.1 Hz), 2.69(br d, 1H, J=13.5 Hz), 1.91(quint, 2H, J=6.5 Hz), 0.90(s, 9H), 0.86(s, 9H), 0.10–0.02(m, 12H).

$^{13}$C-NMR(125 MHz, CDCl$_3$) δ: 167.0(s), 156.8(s), 149.9 (s), 148.7(s), 128.4(d), 127.7(d), 127.6(d), 116.0(d), 113.1 (t), 83.9(d), 73.5(d), 73.0(t), 68.7(d), 68.4(t), 67.7(t), 51.1 (q), 34.2(t), 30.7(t), 25.9(q), 18.3(s), 18.2(s), −4.67(q), −4.72 (q), −4.89(q).

MS m/z:91(100%), 533(M$^+$−57).

HRMS Calcd. for C$_{45}$H$_{45}$O$_6$Si$_2$ (M$^+$−57) 533.2755, Found 533.2751.

The whole content of Japanese Patent Application No. 10-47120, on which the claim for the priority of the present application is based, is incorporated herein by reference.

Industrial Applicability

Compounds of the present invention are novel and are useful intermediates for synthesizing vitamin D derivatives having a substituent at the 2-position, in particular, those vitamin D derivatives which have a 3-hydroxypropoxy group at the 2-position and which exhibit useful physiological activities.

What is claimed is:

1. A compound of the general formula (1):

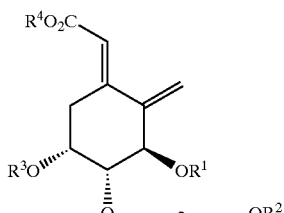
(1)

(wherein $R^1$, $R^2$ and $R^3$, which may be the same or different, represent a hydrogen atom or a protecting group and $R^4$ represents a lower alkyl group).

2. A compound of claim 1, wherein $R^4$ is a methyl group.

3. A process for producing a compound of the general formula (1):

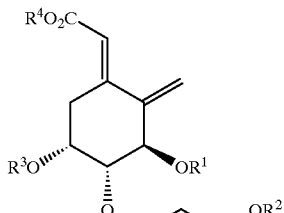
(1)

(wherein $R^1$, $R^2$ and $R^3$, which may be the same or different, represent a hydrogen atom or a protecting group and $R^4$ represents a lower alkyl group) comprising:

(a) reacting a compound of the general formula (3):

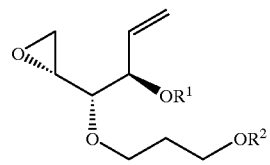
(3)

(wherein $R^1$ and $R^2$, which may be the same or different, represent a hydrogen atom or a protecting group) with a metal acetylide to obtain a compound of the general formula (2):

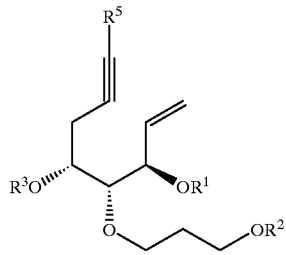
(2)

(wherein $R^1$, $R^2$ and $R^3$, which may be the same or different, represent a hydrogen atom or a protecting group; and $R^5$ represents a hydrogen atom);

(b) reacting the compound of the general formula (2) with a lower alkyl halogenated carbonate to obtain a compound of the general formula (2) (wherein $R^1$, $R^2$ and $R^3$, which may be the same or different, represent a hydrogen atom or a protecting group; and $R^5$ represents a lower alkoxycarbonyl group); and (c) subjecting the compound of the general formula (2) obtained in the step (b) to a reaction of ring formation.

4. The method of claim 3 wherein said metal acetylide is lithium acetylide.

* * * * *